United States Patent [19]

Kulekov et al.

[11] 4,283,628
[45] Aug. 11, 1981

[54] APPARATUS FOR THE CONTROL OF SELF-PROPELLED GAMMA-FLAW DETECTOR

[75] Inventors: Stefan I. Kulekov; Alexander S. Pavlov, both of Sofia, Bulgaria

[73] Assignee: DSO "Montaji"—Kontrolno Zavarachno Upravlenie, Sofia, Bulgaria

[21] Appl. No.: 14,690

[22] Filed: Feb. 23, 1979

Related U.S. Application Data

[63] Continuation-in-part of Ser. No. 908,766, May 23, 1978, abandoned, which is a continuation of Ser. No. 746,291, Dec. 1, 1976, abandoned.

[51] Int. Cl.³ ............................................ G01N 23/00
[52] U.S. Cl. .................................. 250/358 P; 250/360
[58] Field of Search .............. 250/308, 358 R, 358 P, 250/359, 360

[56] References Cited

U.S. PATENT DOCUMENTS 4,006,359  2/1977  Sullins et al. ...................... 250/358 P

FOREIGN PATENT DOCUMENTS 747105  8/1970  Belgium .

Primary Examiner—Davis L. Willis
Assistant Examiner—Janice A. Howell
Attorney, Agent, or Firm—Karl F. Ross

[57] ABSTRACT

A self-propelled device movable inside a pipeline for the radiographic detection of flaws in its weld joints comprises a reversible drive motor and a normally deactivated radiation emitter. Logical circuitry aboard the device, including a two-stage memory, enables the selective energization of the drive motor and the activation of the radiation emitter during standstill in response to command pulses of different duration transmitted from an external radiation source through the pipeline wall and intercepted by one of two sensors.

7 Claims, 2 Drawing Figures

APPARATUS FOR THE CONTROL OF SELF-PROPELLED GAMMA-FLAW DETECTOR

CROSS-REFERENCE TO RELATED APPLICATIONS

This is a continuation-in-part of our copending application Ser. No. 908,766 filed 23 May 1978 as a continuation of prior application Ser. No. 746,291 filed 1 December 1976, both now abandoned.

FIELD OF THE INVENTION

Our present invention relates to a self-propelled device for the radiographic testing of weld joints in a pipeline.

BACKGROUND OF THE INVENTION

Such self-propelled devices, also referred to as pipeline crawlers, are well known per se. They generally comprise reversible propulsion means energizable from without to advance or retract a mobile carrier inside a pipeline whose weld joints are to be tested by means of a normally deactivated radiation emitter aboard the carrier which is trainable upon these joints for panoramically illuminating same. Any flaw in the weld structure will show up on a radiation-sensitive strip surrounding the joint on the outer pipeline surface.

Earlier devices of this character utilized so-called umbilical cords connected outside the pipeline to a source of control signals. U.S. Pat. No. 4,006,359 describes a pipeline crawler responsive to commands transmitted through the pipeline in the form of pulses of radiant energy picked up by sensors aboard the device.

OBJECT OF THE INVENTION

The object of our present invention is to provide a self-propelled flaw detector of the type last referred to, lacking an umbilical cord, which is of simple construction and readily responds to a variety of radiated commands in the form of control pulses of different duration.

SUMMARY OF THE INVENTION

In accordance with our present invention, this object is achieved by the provision of a memory aboard the carrier switchable between a normal or quiescent state and one or more off-normal or operational states by sensing means responsive to command pulses of external radiation transmitted through the pipeline wall, a first signal channel jointly controlled by the sensing means and by the memory for activating the radiation emitter in response to a command pulse of predetermined minimum duration and in the de-energized condition of the propulsion means, and a second signal channel for respectively de-energizing and energizing the propulsion means in the normal and at least one off-normal state of the memory. The first signal channel includes pulse-with-discriminating means for making same nonresponsive to command pulses of less than the aforementioned minimum duration, serving only to switch the memory; the activation of the radiation emitter is terminated by timing means connected between this channel and the memory for switching the latter once more at the end of the desired irradiation period. The pulse-with-discriminating means may comprise a delay line in one of the inputs of a coincidence circuit, preferably a NOR gate, forming part of the first channel.

Thus, a short command pulse insufficient to activate the radiation emitter energizes the propulsion means to set the device in motion. Upon arriving at a weld joint to be inspected, a command pulse outlasting the measuring interval of the delay line causes another switchover of the memory to arrest the device whereupon the radiation emitter is activated (as by being extracted from a holder in which it is normally concealed) for the irradiation period established by the timing means. At the end of this period, concurrently with the deactivation of the radiation emitter, the memory automatically restarts the motion of the carrier inside the pipeline.

In a preferred embodiment, the propulsion means is of the reversible kind and can be selectively energized by the second signal channel or by a third channel for either advancing or retracting the carrier, depending upon the state of the memory. For this purpose, as more fully described hereinafter, the memory may have a further off-normal state reachable by one-time pulsing of a backward-driving sensor, by iterative pulsing of a forward-driving sensor or under the control of the timing means at the end of the irradiation period.

Advantageously, such a memory consists of two cascaded stages of the bistable type which, upon triggering of the first stage by successive command pulses, energize their respective stage outputs in four different binary patterns representing the aforementioned normal or quiescent and off-normal or operational states including an intermediate or neutral state occurring after the first off-normal one. In the intermediate off-normal state, as in the normal one, the two signal channels serving for forward and backward driving are both de-energized so that the carrier vehicle is held stationary within the pipeline. We also prefer to provide these two signal channels with blocking means, e.g. in the form of terminal NOR gates, connected to the two sensors for preventing energization of the propulsion means in either sense as long as a command pulse is being detected.

BRIEF DESCRIPTION OF THE DRAWING

The above and other features of our invention will now be described in detail with reference to the accompanying drawing in which.

SPECIFIC DESCRIPTION

Figure 1:
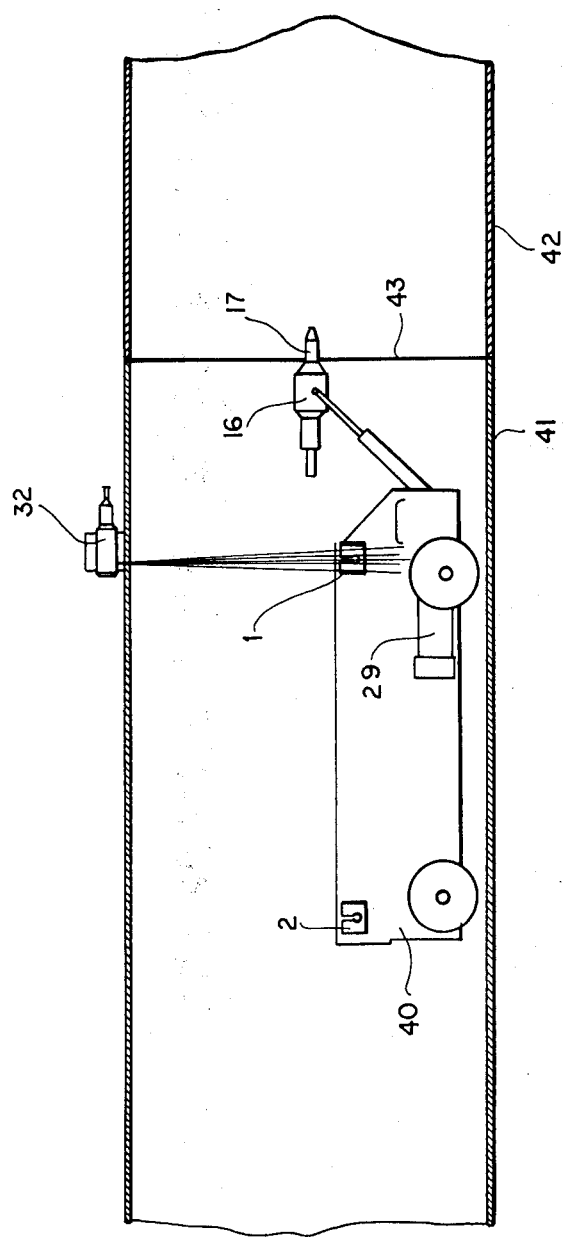
FIG. 1 is an axial sectional view of part of a pipeline, showing a self-propelled device according to our invention operatively positioned therein.

FIG. 1 shows two sections 41, 42 of a pipeline adjoining each other along a weld seam 43. A self-propelled carrier vehicle 40 according to our invention, movable within the pipeline as more fully described hereinafter, supports a front sensor 1 and a rear sensor 2 responsive to low-power radiation from an external source 32 penetrating the pipeline wall. Source 32 may be a portable isotope holder which is temporarily positioned at a location near a joint to be tested, for the purpose of delivering longer or shorter command pulses to one of the sensors of the vehicle. It will be understood, however, that the source 32 could also be a selectively activable radiator controlled from a remote operator's post.

A reversible drive motor 29 aboard the vehicle 40 may be energized in a forward or in a backward mode to advance or to retract the vehicle inside the pipeline. The vehicle carries a holder 16 for a radiation emitter 17 which, in its illustrated extended position, serves to irradiate the weld joint 43 along its entire periphery to test same for possible flaws in a manner well known per se. Holder 16 includes means (e.g. a solenoid) for activating the normally retracted isotope 17 by extracting it from its housing.

Figure 2:
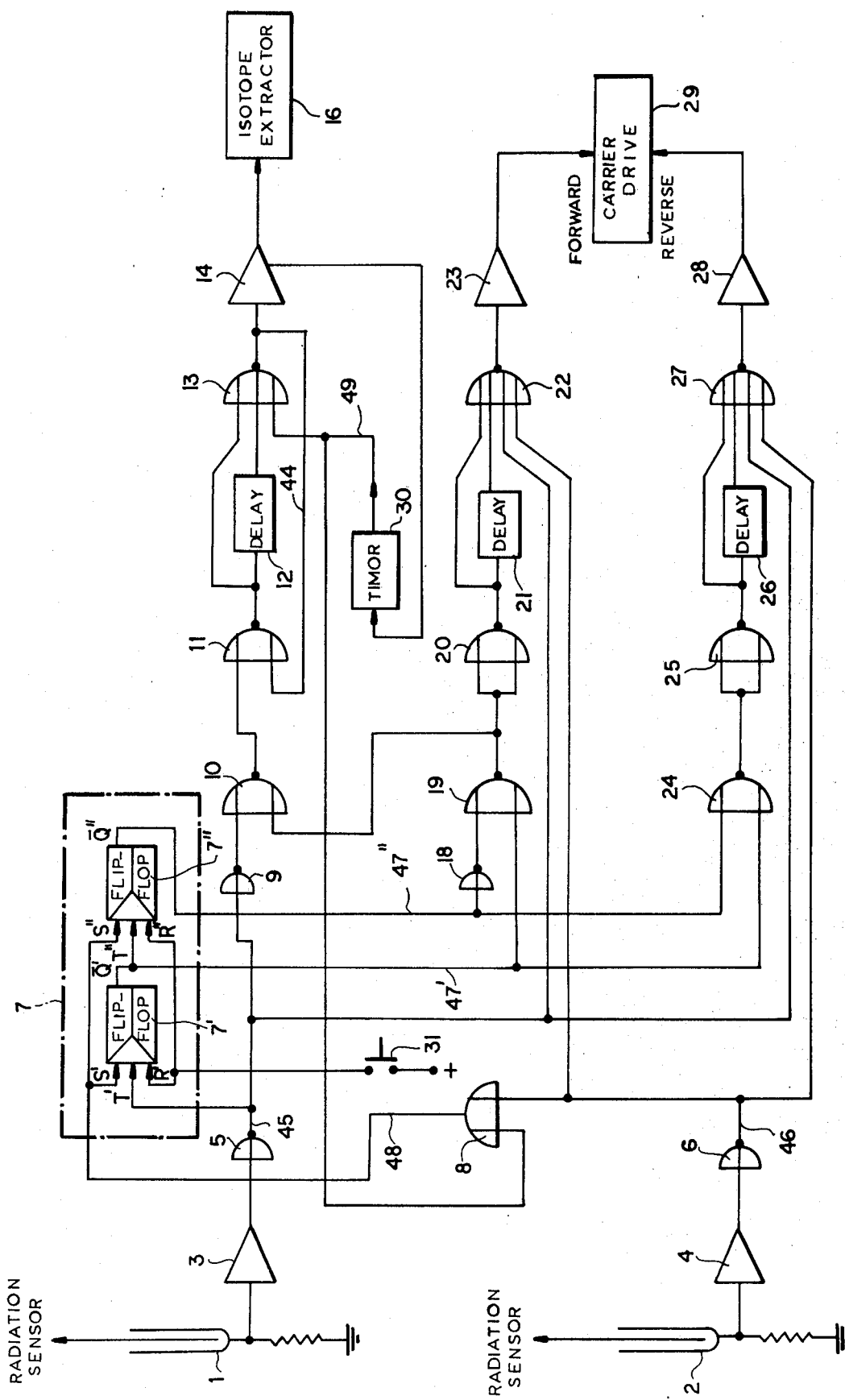
FIG. 2 is a circuit diagram of a system for the control of the device shown in FIG. 1.

The two radiation sensors 1 and 2, which may be Geiger-Müller tubes, are shown in FIG. 2 connected to the inputs of respective amplifiers 3 and 4 working into associated inverters 5 and 6. It will be understood that, in conformity with the usual procedure, tubes 1 and 2 normally have a high-voltage output which drops to substantially zero in the presence of incident radiation. Thus, output leads 45, 46 of inverters 5 and 6 are normally de-energized.

A two-stage memory 7, consisting of a pair of cascaded flip-flops 7' and 7", is triggerable by sensor 1 via a connection extending from lead 45 to a switching input T' of stage 7'. A reset output $\bar{Q}'$ of this stage is connected to a similar switching input T" of stage 7" for reversing same whenever stage 7' is reset; stage 7" has a reset output $\bar{Q}''$. These stages also have respective setting inputs S', S", connected to an output lead 48 of an OR gate 8, and resetting inputs R', R" which can be manually energized via a switch 31 (e.g. a pushbutton) at the beginning of operations, i.e. just before the insertion of the vehicle 40 (FIG. 1) into a pipeline to be inspected.

Also shown in FIG. 2 are three signal channels, i.e. a first channel including an amplifier 14 for activating the isotope extractor 16, a second channel including an amplifier 23 for energizing the reversible drive motor 29 in a forward mode, and a third channel including an amplifier 28 for energizing the drive motor 29 in the reverse mode. All three channel amplifiers are fed by logic networks of the same general structure facilitating their assembly from like modular components.

The isotope-activating channel comprises another inverter 9 inserted between lead 45 and one input of a NOR gate 10 in cascade with two further NOR gates 11, 13 which together constitute a one-bit store of a type known per se. Two inputs of NOR gate 13 are connected to the output of NOR gate 11 by a pair of parallel leads, one of them including a delay line 12; the output of NOR gate 13 has a feedback connection 44 to the second input of NOR gate 11. A third input of NOR gate 13 is connected to an output lead 49 of a timer 30 for delayed energization by a collateral output of amplifier 14 whenever the latter becomes conductive; lead 49 is also connected to one of the inputs of OR gate 8 whose other input is tied to the output lead 46 of inverter 6.

Stage outputs Q' and Q" of flip-flops 7' and 7" are connected to respective leads 47' and 47" extending in parallel to respective inputs of NOR gates 19 and 24 which form part of the forward-driving and reverse-driving channels terminating at amplifiers 23 and 28, with interposition of an inverter 18 between lead 47" and gate 19. The output of NOR gate 19 is connected to the second input of NOR gate 10 and, in parallel therewith, to both inputs of a NOR gate 20 which is the modular counterpart of gate 11 but operates simply as an inverter. A similar NOR gate 25 is connected as an inverter to the output of NOR gate 24. Two final NOR gates 22 and 27 just ahead of amplifiers 23 and 28, respectively, are each provided with two inputs joined to the outputs of the associated inverter 20, 25 in a manner analogous to the connection between gates 11 and 13, i.e. with interposition of a delay line 21 or 26 in one of the two parallel input leads. Gates 22 and 27 have further inputs connected directly to leads 45 and 46.

OPERATION

With the two memory stages 7' and 7" initially reset by a brief closure of switch 31, as described above, memory 7 is in its normal or quiescent state in which NOR gates 19 and 24 are cut off so that amplifiers 23 and 28 are de-energized and drive motor 29 is at standstill. After manual introduction of the vehicle 40 into the pipeline 41, 42, forward propulsion is started by a brief irradiation of sensor 1 with the aid of low-power source 32, for example. The resulting energization of lead 45 establishes a first off-normal or operational state by setting the flip-flop 7' so that voltage on lead 47' disappears. This causes conduction of NOR gate 19 which, on the one hand, makes the NOR gate 10 unswitchable and, on the other hand, cuts off the inverter 20. The blocking of gate 10 prevents any energization of amplifier 14 at this time, regardless of the duration of the command pulse detected by sensor 1. Upon disappearance of that pulse, and after the delay period introduced by line 21, NOR gate 22 conducts and energizes the drive motor 29 via amplifier 23.

When the vehicle 40 arrives at its first stop, e.g. in front of the seam 43 shown in FIG. 1, sensor 1 is irradiated by the source 32 positioned there. Voltage on lead 45 immediately cuts off the NOR gate 22 and arrests the motor 29 while memory stage 7' is reset and sets the stage 7" whereby the memory 7 is triggered into a neutral off-normal or intermediate state in which the pattern of energization of leads 47' and 47" is reversed. NOR gate 19 now has voltage on both inputs and is therefore cut off, enabling the conduction of NOR gate 10 in the presence of the command pulse from source 32; NOR gate 24 also continues blocked by voltage on lead 47'. Unless source 32 is promptly removed or deactivated, NOR gate 11 is closed for a period long enough (e.g. 8 to 10 seconds) to outlast the delay of line 12 so that NOR gate 13 becomes conductive and energizes the isotope extractor 16 via amplifier 14. The ensuing irradiation of the weld joint 43 lasts for an interval determined by timer 30, i.e. until the latter emits a pulse on lead 49 reblocking the NOR gate 13 and returning the one-bit store 11–13 to its normal condition. The same pulse, transmitted by OR gate 8 to lead 48, reaches the setting inputs S' and S" of the memory stages which are therefore switched from their neutral state to a further off-normal or operational state wherein neither of leads 47' and 47" carries voltage. This causes conduction of NOR gate 24 and cuts off the inverter 25, yet NOR gate 27 cannot conduct even after the delay period of line 26 since it is still blocked by the command pulse on lead 45.

If the operator now simply removes or deactivates the source 32, amplifier 28 will energize the drive motor 29 in the reverse mode to retract the vehicle 40 from the pipeline. If, however, sensor 1 is now briefly pulsed two more times, memory 7 is switched through its normal state to the first off-normal state provided for forward drive so that the vehicle may advance to the next weld joint for testing same or, possibly, to the opposite end of the pipeline for exiting therefrom.

A reverse drive may also be initiated, whatever the state of memory 7, by irradiation of sensor 2 to energize the lead 46. This energization sets the two memory stages 7', 7", by way of OR gate 8 and lead 48, in the same manner as when that OR gate passes a pulse from timer 30 after the irradiation of a weld joint. The voltage on lead 46 also immediately cuts off the NOR gate 22, in the event that the vehicle had been in forward motion, and inhibits the NOR gate 27 so that the reverse drive cannot start until the command pulse has terminated.

When the memory 7 is in its first off-normal state characterized by voltage on lead 47" i.e. when its first stage 7' has been set, but not on lead 47', a short command pulse delivered to sensor 1, of insufficient duration to trip the isotope extractor 16, will establish the neutral state in which lead 47' is energized to the exclusion of lead 47", thereby preventing or arresting the forward motion of the vehicle. A single irradiation of either sensor will then initiate a reverse motion of the vehicle, yet resumption of forward motion could be brought about by three successive command pulses applied only to sensor 1. The first of these three pulses, which establishes the third off-normal memory state characterized by the de-energization of both leads 47' and 47" due to a setting of both stages 7' and 7", should be short and should be followed immediately by the second pulse within the delay period of line 26 to prevent the start of backward motion in this instance.

It will thus be seen that we have provided a system for controlling both the motion of a pipe crawler and the operation of its radiation emitter by simple logical circuitry responsive to external pulses of greater or lesser duration. The described operations could be performed even without the rear sensor 2, though the aforementioned irradiation of sensor 2 for a direct reversal of the vehicle motion without activation of the radiation emitter 17 is a distinct advantage since it enables a quick retraction of the vehicle from the pipeline if this should become necessary.

We claim:

1. In a device for the radiographic testing of weld joints in a pipeline, including a normally deactivated radiation emitter trainable upon a weld joint, a self-propelled carrier for said radiation emitter, and propulsion means on said carrier for driving same inside a pipeline to be inspected, the combination therewith of equipment aboard said carrier comprising:

sensing means responsive to external radiation transmitted through the pipeline wall;

memory means adapted to assume several different states, including a quiescent state and at least one operational state, and connected to said sensing means for switchover from one state to another by command pulses of said external radiation;

a first signal channel jointly controlled by said memory means for activating said radiation emitter in response to a command pulse of predetermined minimum duration in a de-energized condition of said propulsion means;

a second signal channel controlled by said memory means for de-energizing and energizing said propulsion means in said quiescent state and said operational state, respectively, of said memory means;

pulse-width-discriminating means in said first signal channel for making same nonresponsive to command pulses of less than said minimum duration, said pulse-width-discriminating means including a logical coincidence circuit with a pair of parallel inputs and delay means in series with one of said parallel inputs; and timing means connected between said first signal channel and said memory means for switching the latter to deactivate said radiation emitter after a predetermined irradiation period.

2. The combination defined in claim 1 wherein said propulsion means is reversible and is energizable via said second signal channel in a forward-driving mode, further comprising a third signal channel controlled by said memory means for energizing said propulsion means in a backward-driving mode in a further operational state of said memory means.

3. The combination defined in claim 2 wherein said sensing means comprises a first radiation sensor connected to a triggering input of said memory means for sequentially switching same through all the states thereof, in response to successive command pulses detected by said first sensor, and a second radiation sensor connected to a setting input of said memory means for establishing said further operational state thereof in response to a command pulse detected by said second sensor.

4. The combination defined in claim 2 or 3 wherein said timing means is connected to said setting input for establishing said further operational state concurrently with the deactivation of said radiation emitter.

5. The combination defined in claim 2 or 3 wherein said memory means comprises two cascaded stages establishing said one operational state, an intermediate state, said further operational state and said quiescent state in response to successive command pulses detected by said first sensor, said second and third signal channels being both de-energized in said quiescent and intermediate states.

6. The combination defined in claim 2 wherein said second and third signal channels are provided with delay means for retarding the energization of said propulsion means and with blocking means connected to said first and second sensors for preventing such energization in the presence of a command pulse.

7. The combination defined in claim 1 or 2 wherein said coincidence circuit comprises a NOR gate.

* * * * *